United States Patent [19]

Hirao et al.

[11] Patent Number: 5,057,695
[45] Date of Patent: Oct. 15, 1991

[54] METHOD OF AND APPARATUS FOR MEASURING THE INSIDE INFORMATION OF SUBSTANCE WITH THE USE OF LIGHT SCATTERING

[75] Inventors: Konomu Hirao, Ibaraki; Naoki Inamoto, Higashiosaka, both of Japan

[73] Assignee: Otsuka Electronics Co., Ltd., Osaka, Japan

[21] Appl. No.: 450,980

[22] Filed: Dec. 15, 1989

[30] Foreign Application Priority Data

Dec. 19, 1988 [JP] Japan .................................. 63-320083

[51] Int. Cl.$^5$ ............................................ G01N 21/49
[52] U.S. Cl. ...................................... 250/575; 356/41; 128/633
[58] Field of Search .................. 250/221, 575; 356/40, 356/41, 39, 42; 128/633, 634, 664, 665, 666

[56] References Cited

U.S. PATENT DOCUMENTS

| | | | |
|---|---|---|---|
| 3,638,640 | 2/1972 | Shaw | 128/2 R |
| 4,223,680 | 9/1980 | Jobsis | 128/633 |
| 4,621,643 | 11/1986 | New, Jr. et al. | 128/633 |
| 4,714,080 | 12/1987 | Edgar, Jr. et al. | 128/666 |
| 4,819,752 | 4/1989 | Zelin | 356/41 |
| 4,846,183 | 7/1989 | Martin | 356/41 |
| 4,907,594 | 3/1990 | Muz | 128/664 |

FOREIGN PATENT DOCUMENTS 104772 4/1984 European Pat. Off. .
286142 10/1988 European Pat. Off. .

Primary Examiner—Davis L. Willis
Assistant Examiner—Que T. Le
Attorney, Agent, or Firm—Sughrue, Mion, Zinn, Macpeak & Seas

[57] ABSTRACT

The present invention utilizes the difference of light reception data generated based on the difference in length of substantial optical diffusion paths between a single light receiving point and a plurality of irradiation points, or between a plurality of light receiving points and a single irradiation point. According to the present invention, the inside information of substance based on the difference in length of the optical diffusion paths, may be measured. Even though measurements are made under different measuring conditions as to the part to be measured, the measuring time, etc., there may be obtained reliable measured data of the inside information with good reproducibility.

8 Claims, 10 Drawing Sheets

WAVE LENGTH (nm)

1

METHOD OF AND APPARATUS FOR MEASURING THE INSIDE INFORMATION OF SUBSTANCE WITH THE USE OF LIGHT SCATTERING

BACKGROUND OF THE INVENTION

The present invention relates to a method of and the apparatus for measuring the inside information of substance with the use of light scattering, in which light is irradiated from the surface of substance into the inside thereof and, after the light is diffused inside of the substance, the light is received at one point on the substance surface, thereby to measure variations of the light intensity according to the nature of the inside of the substance.

When the degree of oxygen saturation of the blood or the tissue of a predetermined part of a living body is measured, it is possible to know the reduction or oxidation condition of hemoglobin (Hb) of the blood in the tissue. Based on such a condition, the metabolism of the organ may be evaluated.

In this connection, there have been proposed a variety of methods of properly measuring the degree of oxygen saturation above-mentioned. Of these, public attention has been recently attracted to an optical method capable of executing such a measurement without injury of a living body. According to this optical measuring method, near-infrared rays less dangerous to a living body are irradiated to a living body and, after being diffused or scattered in the living body, the light is received to measure the composite light absorptivity by oxyhemoglobin ($HbO_2$) and reduced hemoglobin (Hb) in the living body. According to this method, the component ratio of $HbO_2$ to Hb may be acquired.

More specifically, the molecular absorption coefficients of $HbO_2$ and Hb at each wavelength differ from each other. The composite molecular absorption coefficient of $HbO_2$ and Hb of the living body at each wavelength is regarded as a value ranged between the molecular absorption coefficient of $HbO_2$ and the molecular absorption coefficient of Hb. By measuring such a value, an approximate component ratio of $HbO_2$ to Hb may be presumed. For example, when this value is in the vicinity of the molecular absorption coefficient of $HbO_2$, it means that $HbO_2$ is a dominant component. On the other hand, when this value is in the vicinity of the molecular absorption coefficient of Hb, it means that Hb is a dominant component.

However, this method cannot eliminate the influence of the total amount of hemoglobin exerted upon the molecular absorption coefficients. Accordingly, the isobestic point of light absorption spectra of $HbO_2$ and Hb is used as a standard.

More specifically, the light absorption spectra of $HbO_2$ and Hb present an isobestic point in the vicinity of 800 nm as shown in FIG. 12. In the area of wavelength longer than 800 nm, the molecular absorption coefficient of $HbO_2$ is greater than the molecular absorption coefficient of Hb, while in the area of wavelength shorter than 800 nm, the molecular absorption coefficient of Hb is greater than the molecular absorption coefficient of $HbO_2$. By measuring the molecular absorption coefficients at other wavelengths with the molecular absorption coefficients at the isobestic point serving as standards, the component ratio of $HbO_2$ to Hb, i.e., the degree of oxygen saturation of blood may be acquired regardless of the amount of measured blood. There exist an equibestic pair and a contrabestic pair before and after the isobestic point. When the molecular absorption coefficients at these points are measured, the blood condition may be acquired with better precision (See Japanese Patent Publication No. 11614/1983).

According to a conventional measuring method, for example, as disclosed in the Publication above-mentioned, the end surfaces of two condensing fibers respectively come in contact with two points of the surface of a living body, and the reflected light or transmitted light of the light irradiated into the living body from one condensing fiber is received by the other condensing fiber. The light thus received is detected and converted, by a photosensor, into an electric signal, which is then subjected to a processing.

This method presents the following problems.

That is, it is difficult to cause the condensing fibers to accurately come in contact with a predetermined part of a living body at each measurement. As a matter of fact, the fiber contact points are always positionally shifted from the parts of a living body with which the fibers should come in contact. By such positional deviation, variations of the nature (such as the skin color, the amount of subcutaneous fat) peculiar to the measured part are disadvantageously entered. This deteriorates the reproducibility of the measurement results.

SUMMARY OF THE INVENTION

It is an object of the present invention to provide a method of and the apapratus for measuring the inside information of substance with the use of light scattering, capable of achieving a reliable measurement with good reproducibility regardless of the difference of a variety of measuring conditions, such as the difference of points to be measured.

To achieve the object above-mentioned, the method of measuring the inside information of substance with the use of light scattering in accordance with the present invention, comprises the steps of:

successively irradiating lights at a plurality of irradiation points which are disposed substantially in the same direction with respect to a light receiving point on the surface of substance, the substantial optical diffusion paths from the irradiation points to the light receiving point being different in length from one another;

receiving the irradiated lights at the light receiving point;

executing a predetermined calculation based on the difference of light reception data corresponding to the respective irradiations; and measuring the inside information of the substance.

To achieve the object above-mentioned, the apparatus for measuring the inside information of substance with the use of light scattering in accordance with the present invention, comprises:

light irradiating means for irradiating lights at a plurality of irradiation points disposed substantially in the same direction with respect to a light receiving point on the surface of substance, the substantial optical diffusion paths from the irradiation points to the light receiving point being different in length from one another;

light receiving means for receiving the irradiated lights at the light receiving point; and data processing means for executing a predetermined calculation based on the difference of light reception data, thereby to supply the inside information of the substance.

The positional relationship of the light receiving point and the irradiation points may be reverse. More specifically, light may be irradiated from an irradiation point on the surface of substance, and the light may be received at a plurality of light receiving points disposed substantially in the same direction with respect to the irradiation point, the substantial optical diffusion paths from the irradiation point to the light receiving points being different in length from one another.

In the foregoing, the term "substantial optical diffusion path" refers to the locus of the center points or average points of the energy distributions of a luminous flux when a number of lights (photons) advance from a fixed point in substance or on the surface thereof and reach another fixed point while scattering and diffusing in the substance. The expression "the substantial optical diffusion paths being different in length from one another" refers the state where the substantial optical diffusion paths between the irradiation points and the light receiving point are different in length from one another, whether the physical distances therebetween are the same, or different from one another.

According to the method of and the apparatus for measuring the inside information of substance with the use of light scattering of the present invention, lights are successively irradiated at a plurality of irradiation points disposed substantially in the same direction with respect to the light receiving point on the surface of substance, the substantial optical diffusion paths to the light receiving point being different in length from one another, and the irradiated lights are received at the light receiving point. In this case, the light reception data at the light receiving point are different from one another due to the difference of the substantial optical diffusion paths between the irradiation points and the light receiving point.

This is because the substantial optical diffusion paths between the irradiation points and the light receiving points are common for the most part thereof, but they become different in length in the vicinity of the irradiation points, since the irradiation points are disposed substantially in the same direction with respect to the light receiving point. Accordingly, by obtaining the difference of light reception data, there may be measured the inside information of the substance based on the difference in length of the optical diffusion paths. In other words, the inside information of the substance in the most part of the optical diffusion paths are cancelled by one another and only the inside information of the substance in the vicinity of the irradiation points may be taken out and measured.

Accordingly, such a cancel operation eliminates the most part of error factors generated along the optical diffusion path in the prior art in which light irradiated from a single irradiation point is received at a single light receiving point. Thus, the inside information of the substance only in the vicinity of the irradiation points may be taken out with high precision and good reproducibility.

As described in the foregoing, the method of and apparatus for measuring the inside information of substance with the use of light scattering of the present invention, may measure the inside information of substance with the use of the difference of light reception data generated by the difference in length of the substantial optical diffusion paths between a single light receiving point and a plurality of irradiation points, or between a plurality of light receiving points and a single irradiation point. Accordingly, there may be obtained reliable measured data of inside information with good reproducibility even though measuring conditions of the substance such as the parts to be measured are different from one another.

Even though the positional relationship between the light receiving point and the irradiation points is reverse, the inside information of the substance in the most part of the optical diffusion paths may be cancelled by one another and the inside information of the substance only in the vicinity of the light receiving point may be taken out. Thus, the similar operational results may be obtained.

The features above-mentioned of the present invention will be apparent from the following description with reference to the attached drawings.

DESCRIPTION OF THE PREFERRED EMBODIMENTS

The following description will discuss in detail the present invention with reference to the attached drawings showing embodiments of the invention.

Figure 1:
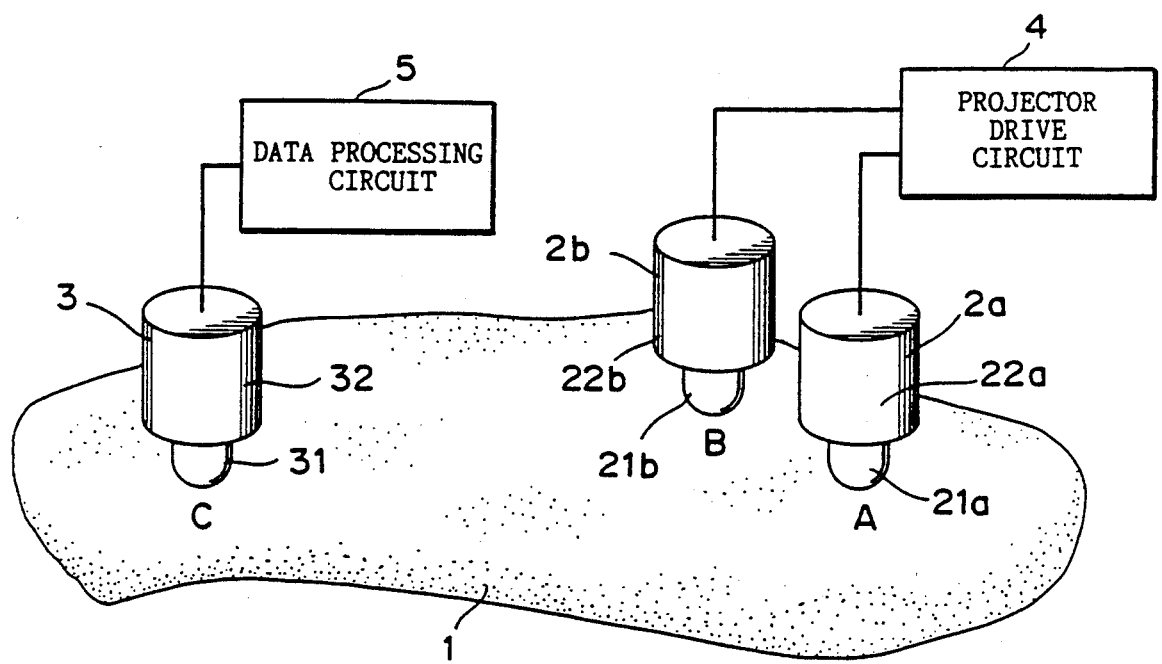
FIG. 1 is a schematic perspective view of a first embodiment of the present invention in which a single light receiving point and a plurality of light irradiation points are disposed on the surface of substance.

FIG. 1 is a view illustrating a basic embodiment of the present invention. In FIG. 1, there are disposed projectors 2a, 2b and a light receiver 3 for receiving the lights passing through a living body after irradiated from the projectors 2a, 2b, the projectors 2a, 2b and the receiver 3 facing the interface 1 of tissue of a living body. The irradiation points A, B of the projectors 2a, 2b are disposed substantially in the same direction with respect to the light receiving point C of the light receiver 3 such that the irradiation point B as opposed the irradiation point A, is closer to the light receiving point C. The distances between the light receiving point C and each of the irradiation points A, B are properly set such that the sensitivities of the lights received by the light receiver 3 are detected and influences of the reflected light from the interface 1 of the living body tissue are disregarded. More specifically, if the light receiving point C is excessively separated from the irradiation points A, B, the intensities of the lights entering into the light receiver 3 from the projectors 2a, 2b are weakened to deteriorate the measurement SN ratio. If the light receiving point C is excessively close to the irradiation points A, B, the lights irradiated from the projectors 2a, 2b are reflected directly from the living body tissue interface 1 and enter into the light receiver 3. This causes the measurement signals to be relatively weakened. To exclude the influence of such reflected light, it is preferable that the directivities of the projectors 2a, 2b and the light are set as narrow as possible. However, if the directivities are too narrow, a major portion of the lights irradiated from the projectors 2a, 2b enters into the inside of the living body. This prevents a sufficient amount of light from reaching the light receiver 3.

The distance AB is shorter than the distance AC between the light receiving point C and the irradiation point A or the distance BC between the light receiving point C and the irradiation point B. If the distance AB is substantially equal to or longer than the distance AC or the distance BC, the result of measurement of the inside information of a living body between the irradiation points A and B is apt to contain an error, as will be discussed later, and no reproducibility of measurements may be assured.

Provision is made such that the projectors 2a, 2b are connected to a projector drive circuit 4 and an electric signal supplied from the light receiver 3 is entered into a data processing circuit 5.

Figure 2:
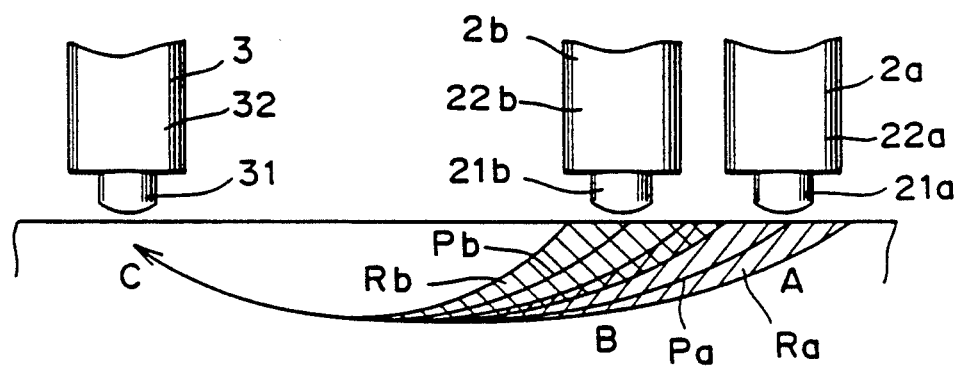
FIG. 2 is a view of optical paths in the embodiment in FIG. 1.

More specifically, the projector 2a comprises (i) a projector body 22a incorporating a light source such as a semiconductor laser, an LED or the like, and (ii) a light guiding member (for example, lens) 21a for guiding the light projected from the light source. Likewise, the projector 2b comprises a projector body 22b and a light guiding member 21b. The light receiver 3 comprises a light receiver body 32 incorporating a photodetector such as a phototransistor or the like, and a light guiding member 31 for guiding the light received from the surface 1, to the photodetector. In the embodiment above-mentioned, condensing fibers or the like may be used as the light guiding members 21a, 21b and 31. In the embodiment above-mentioned, the light guiding members 21a, 21b, 31 face the interface 1 of the living body tissue with gaps provided therebetween (See FIG. 2). However, the light guiding members 21a, 21b, 31 may come in contact with the interface 1 of the living body tissue.

When the projector drive circuit 4 is operated to light the projectors 2a, 2b, the illumination lights enter into the inside of the interface 1. Portions of these lights are transmitted in the inside of the living body, and reach the light receiver 3. More specifically, that portion of the light projected from the projector 2a which may be detected at the light receiving point C, advances while scattering and diffusing inside of the living body. The optical diffusion path where this light advances while diffusing, is shown by a hatched area Ra in FIG. 2. Out of this optical diffusion path Ra, a path pa represents an optical path where a major light portion passes, i.e., an optical path connecting the centers of the entire luminous flux which diffusively advances (which path pa is substantially an optical diffusion path and is hereinafter simply referred to an optical diffusion path). Likewise, an optical diffusion path where the light projected from the projector 2b reaches the light receiving point C, is represented by Rb, and the optical diffusion path of this light is represented by pb.

The irradiation points A, B of the projectors 2a, 2b are disposed substantially in the same direction with respect to the light receiving point C of the light receiver 3, and the distance AB is shorter than the distance AC or the distance BC. Accordingly, the optical diffusion path pa of the light which reaches the light receiver 3 after projected from the projector 2a, is mostly identical with the optical diffusion path pb of the light which reaches the light receiver 3 after projected from the projector 2b. However, as compared with the optical diffusion path pb, the optical diffusion path pa additionally has a path corresponding to the distance AB. Accordingly, as compared with the light which is projected from the projector 2b and reaches the light receiver 3, the light which is projected from the projector 2a and reaches the light receiver 3, additionally contains the inside information of the living body between the irradiation points A and B, particularly the inside information in the vicinity of the surface of the living body. Accordingly, when the light which is projected from the projector 2a and reaches the light receiver 3, is detected and entered into the data processing circuit 5, and the light which is projected from the projector 2b and reaches the light receiver 3, is detected and entered into the data processing circuit 5, and a predetermined calculation is then made based on the difference between both detection signals, the inside information data of the living body between the irradiation points A, B may be obtained.

The difference in intensity between the light which is projected from the projector 2a and reaches the light receiver 3, and the light which is projected from the projector 2b and reaches the light receiver 3, becomes greater as the distance between the irradiation points A and B is greater. Accordingly, the difference between both detection signals becomes greater. As a result, the inside information data of the living body between the irradiation points A and B appear clearly. However, if the distance AB is excessively great, the types and amount of the inside information of the living body between the irradiation points A and B are excessively increased. This causes the information to become rather unclear as measured data. Thus, an excessively long distance AB presents the defect that accurate and reproducible measured data cannot be acquired. It is therefore required to set the distance AB to a proper value.

The following description will discuss a calculating method applied to obtain the inside information of substance, based on the difference between the light data received by the light receiver 3.

Figure 3:
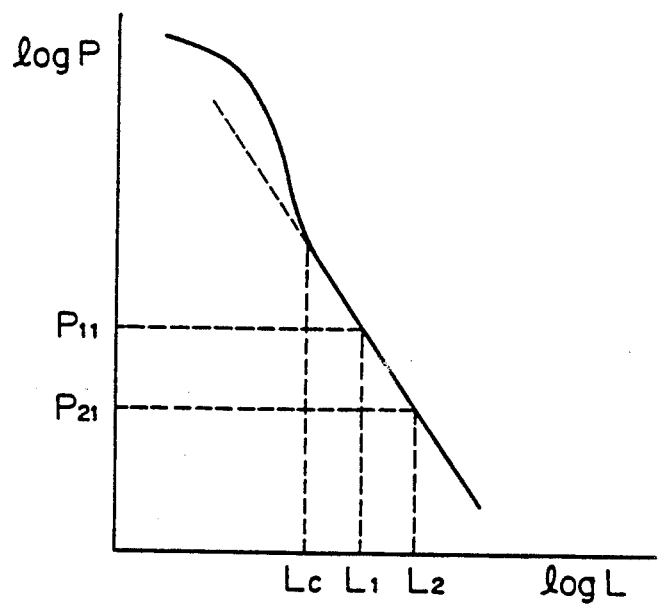
FIG. 3 is a double logarithmic graph illustrating the relationship between a light reception amount and the distance L between a light receiving point and a light irradiation point.

FIG. 3 is a double logarithmic graph illustrating the relationship between a light reception amount (the number of counts by a photomultiplier) P and the distance L between a projector and a light receiver at a predetermined wavelength $\lambda 1$. For a distance shorter than a predetermined distance $L_0$, the light reception amount P presents an expansion in the graph. It is considered that such an expansion is caused by the influence of light reflected from the tissue surface, or the like. When the distance exceeds the predetermined distance $L_0$, the graph presents a substantially linear line. Accordingly, two points L1 and L2 exceeding the predetermined distance $L_0$ are selected and light reception amounts P11 and P21 at these points are measured. When the logarithm of each value is taken, the following linear equations are obtained:

$$\log P11 = a1 \log L1 + b1 \quad (1)$$

$$\log P21 = a1 \log L2 + b1 \quad (2)$$

The difference between both equations is expressed by the following equation:

$$\log (P11/P21) = a1 \log (L1/L2) \quad (3)$$

Measurements at other wavelength λ2 and λ3 are made in the same manner as above-mentioned, and the following equations are obtained:

$$\log (P12/P22) = a2 \log (L1/L2) \quad (4)$$

$$\log (P13/P23) = a3 \log (L1/L2) \quad (5)$$

By eliminating log (L1/L2) in each of the equations (3) to (5), the ratios a1/a2 and a3/a2 may be obtained.

The following description will discuss a percentage absorption method as an example of a method of obtaining molecular concentrations from the ratios a1/a2 and a3/a2.

$$a1 = \frac{(co\,\alpha o1 + cr\,\alpha r1)}{(co + cr)} \quad (9)$$

$$a2 = \frac{(co\,\alpha o2 + cr\,\alpha r2)}{(co + cr)} \quad (10)$$

$$a3 = \frac{(co\,\alpha o3 + cr\,\alpha r3)}{(co + cr)} \quad (11)$$

where co: $HbO_2$ concentration,
αo1: molecular absorption coefficient of $HbO_2$ at λ1,
αo2: molecular absorption coefficient of $HbO_2$ at λ2,
αo3: molecular absorption coefficient of $HbO_2$ at λ3,
cr: Hb concentration,
αr1: molecular absorption coefficient of Hb at λ1,
αr2: molecular absorption coefficient of Hb at λ2, and
αr3: molecular absorption coefficient of Hb at λ3.

When it is now supposed that (co+cr) is equal to 1, the following equations are established:

$$a1 = (co\,\alpha o1 + cr\,\alpha r1) \quad (12)$$

$$a2 = (co\,\alpha o2 + cr\,\alpha r2) \quad (13)$$

$$a3 = (co\,\alpha o3 + cr\,\alpha r3) \quad (14)$$

When it is now supposed that λ2 is the wavelength corresponding to the isobestic point, the following equation is established:

$$\alpha o2 = \alpha r2$$

When αo2 is equal to αr2 which is put to A, a2 then becomes equal to A.

On the other hand, there are being obtained, as the results of spectral measurement, the ratios n1, n2, n3, n4 of the molecular absorption coefficients αo1, αr1, αo3, αr3 at other wavelengths λ1 and λ3, to the molecular absorption coefficient a2 at the wavelength λ2 corresponding to the isobestic point. Then, when denoting the following equations:

$$\alpha o1 = n1A, \quad \alpha r1 = n2A, \quad (15)$$
$$\alpha o3 = n3A, \quad \alpha r3 = n4A$$

the equation (12) is expressed by the following equation:

$$a1 = (n1\,co + n2\,cr)A \quad (16)$$

and the equation (13) is expressed by the following equation:

$$a3 = (n3\,co + n4\,cr)A \quad (17)$$

On the other hand, since the ratios a1/a2 and a3/a2 are being obtained, the Hb concentration cr and the $HbO_2$ concentration co may be obtained from the equations (16) and (17). Then, the degree of oxygen saturation may be obtained.

According to this measuring method, the light irradiated from the irradiation point, expands as if diffusing while repeatedly reflected and refracted, and reaches the light receiving point. It is therefore considered that the actual optical path length is longer than the apparent optical path length. Further, since the living body presents different absorptivities at different wavelengths, the optical paths differ in length dependent on wavelengths.

Accordingly, it is preferable to execute a correction of the average optical path length. Such a correction is, for example, based on the Kubelka-Munk theory that the variation of the average optical path length of a completely diffused light is double the variation of the distance between the irradiation point and the light receiving point. According to this theory, the light reception amount P11 at the distance L1 and the light reception amount P21 at the distance L2 at the same wavelength λ1 satisfy the following equation:

$$P21/P11 = (1-a1)^{2(L2-L1)} \quad (6)$$

Likewise, the following equation is satisfied at the wavelength λ2

$$P22/P12 = (1-a2)^{2(L2-L1)} \quad (7)$$

At the wavelength λ3, the following equation is satisfied:

$$P23/P13 = (1-a3)^{2(L2-L1)} \quad (8)$$

When the percentage absorption method above-mentioned is applied after the correction of the optical path length has been made with the use of these equations, a value closer to the actual value may be obtained.

The present invention is not limited to the embodiment above-mentioned. In the embodiment above-mentioned, lights are successively irradiated at a plurality of irradiation points on the surface of substance and the irradiation lights are received at one light receiving point. However, arrangement may be made such that light is irradiated at one point on the surface of substance and the light is received at a plurality of light receiving points.

Figure 4:
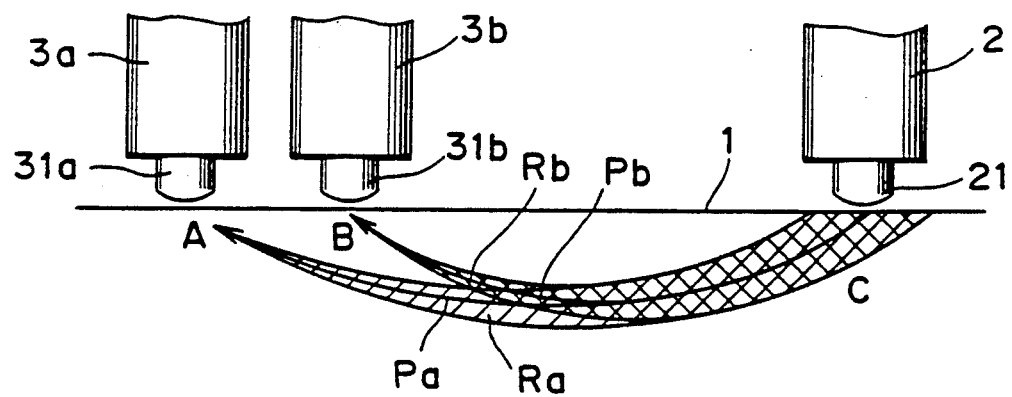
FIG. 4 is a schematic view of optical paths in a second embodiment of the present invention in which a single irradiation point and a plurality of light receiving points are disposed on the surface of substance.

FIG. 4 shows such an arrangement in which light irradiated by a single projector 2 is incident upon light receivers 3a, 3b at the same time. When detection signals of the light receivers 3a, 3b are subjected to the calculation processing as above-mentioned, there may be taken data containing the inside information of a living body between the light receiving points A and B.

Figure 5:
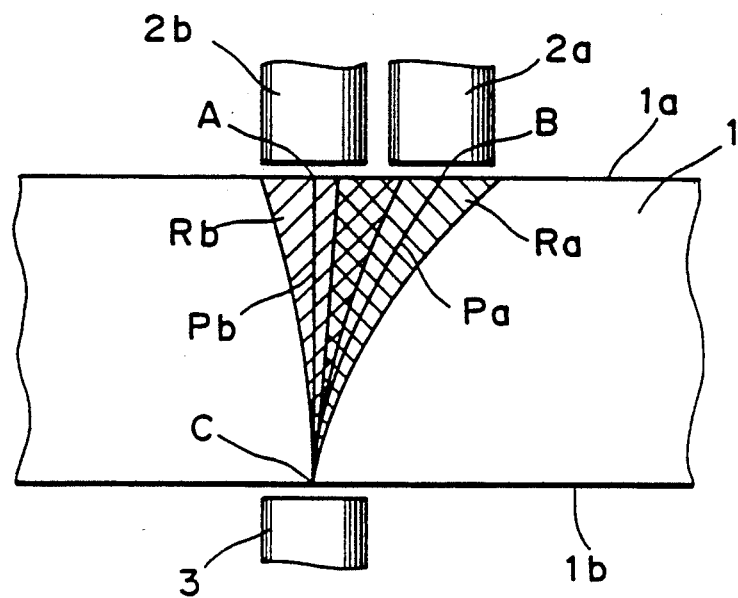
FIG. 5 is a schematic view of optical paths in a third embodiment of the present invention in which irradiation points and a light receiving point are respectively disposed on the opposite surfaces of substance.

As shown in FIG. 5, the present invention may provide apparatus for measuring the inside information of a part of a living body 1 between the opposite surfaces 1a and 1b thereof.

More specifically, projectors 2a, 2b (of which light guiding members are incorporated in the casings of the projectors 2a, 2b) are disposed as facing the surface 1a of a living body, and a light receiver 3 (of which light guiding member is incorporated in the casing of the light receiver 3) is disposed as facing the opposite surface 1b of the living body, the light receiver 3 being adapted to receive the lights which have passed through the living body after irradiated from the projectors 2a, 2b. The distance AB between the irradiation points A and B of the projectors 2a and 2b is much smaller than the thickness of the living body. Accordingly, the optical diffusion path pa and the optical diffusion path pb considerably overlap each other in the inside of the living body and, in particular, in the vicinity of the light receiver 3. In the vicinity of the projectors 2a, 2b where the irradiation points A and B are separated from each other, the optical diffusion paths pa, pb less overlap each other. Thus, there may be obtained the inside information of the living body based on the difference between the optical diffusion paths.

This embodiment is advantageous in that the information of an inner part of substance with respect to the surface thereof is obtained and the influence of light reflected and scattered from the surface is completely disregarded. Accordingly, the directivities of the projectors 2a, 2b and the light receiver 3 may be sharpened and the light amount may be increased. Thus, a thick sample may be measured with good reproducibility.

In the embodiments above-mentioned, the degree of oxygen saturation of hemoglobin in blood is measured. However, the present invention is not limited to such an application. That is, other substance may be measured with the wavelength suitably changed. For example, there may be measured the concentration of dissolved carbon monoxide, carbon dioxide or the like. Further, the embodiments above-mentioned show the arrangements in which two irradiation points or two light receiving points are disposed. However, the present invention is not limited to such arrangements, but may be applied to an arrangement having three or more measuring points to improve the measurement precision.

In the embodiments above-mentioned, a living body is measured. However, the present invention may be applied to measurement of the inside information (type, disease or the like) of food such as fruit, meat, seafood, etc., or plant such as seeds, saplings, etc. It should therefore be understood that a variety of modifications of the present invention may be made without departing from the scope thereof.

EXAMPLE 1

There were used, as the projector, a semiconductor laser having an output of 0.8 mW and a wavelength of 780 nm (isobestic point), and, as the light receiver, a photomultiplier having a condensing fiber. The light irradiation portion of the projector was secured to the surface of an arm of a human being, and the tip of the condensing fiber was applied to another portion of the same arm.

Figure 6:
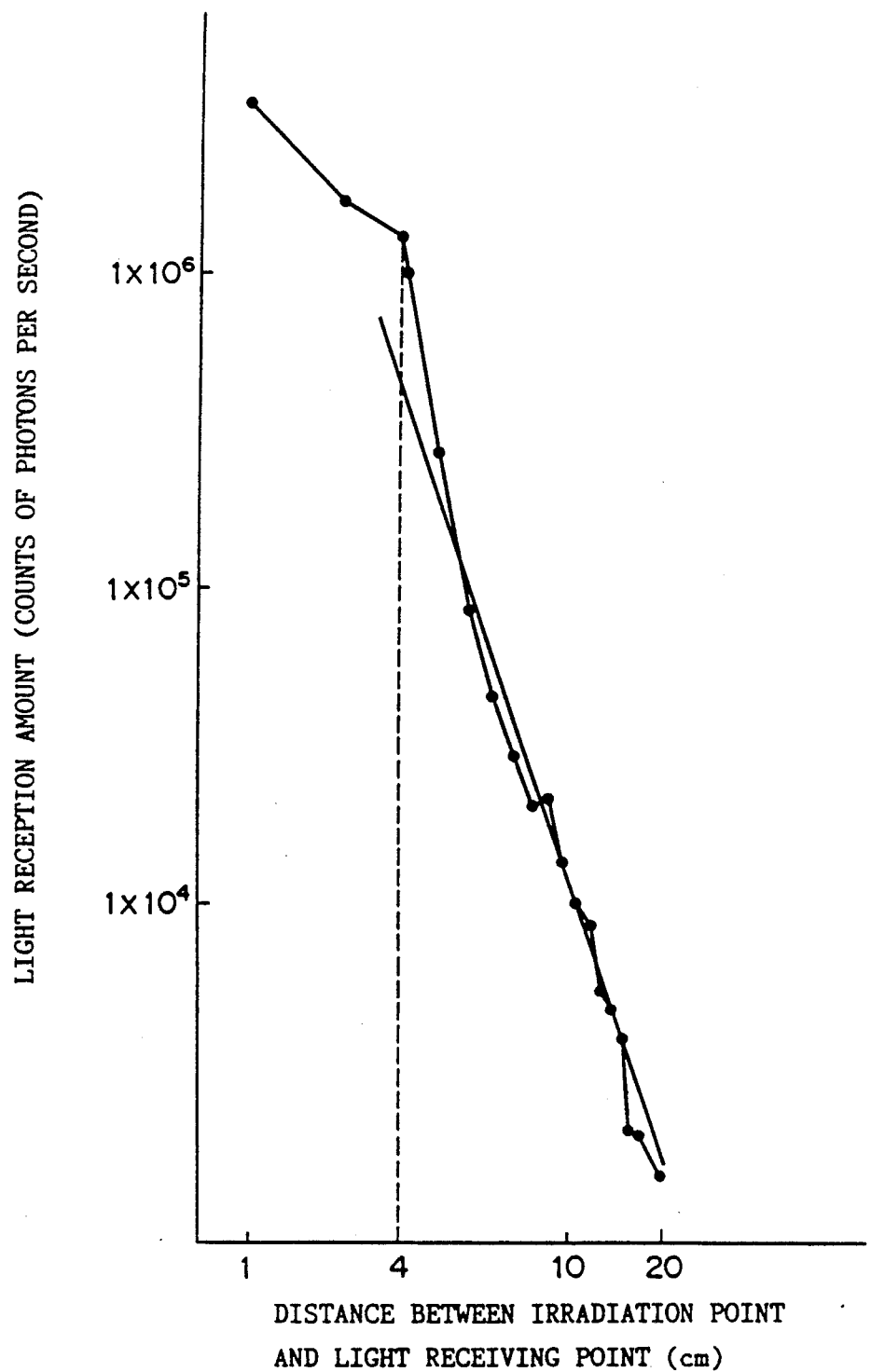
FIG. 6 is a graph illustrating the light reception amount measured with the distance between an irradiation point and a light receiving point varied.

FIG. 6 is a graph in which the light reception amounts (the counted number of photons per second) weres plotted while moving the tip of the condensing fiber. It is understood from FIG. 6 that, when the distance between the irradiation point and the light receiving point is not greater than about 4 cm, the light reception amount presents an expansion which means that the influence of light reflected from the arm surface is exerted. It is therefore required that the distance between the irradiation point and the light receiving point is at least 3 cm or more and, preferably, 4 cm or more. If the distance above-mentioned is excessively longer, the light reception amount is reduced and the influence of noise or the like of the apparatus is exerted. It is therefore preferable to set such a distance less than about 6 cm.

EXAMPLE 2

Two small-size LEDs applied to the same arm of a human being were alternately lighted at predetermined intervals. Likewise in Example 1, a photomultiplier having a condensing fiber was used as the light receiver, and the tip of the condensing fiber was secured as separated by about 4 cm from the contact points of the small-size LEDs. Data were taken while the distance between two LEDs was changed from 0.3 cm to 1 cm. When the distance between the LEDs was about 1 cm, the reproducibility of measurement was lowered under the influence of a variety of factors such as capillary vessels or the like existing between the LED irradiation points. When the distance was in a range from about 0.3 to about 0.5 cm, data excellent in reproducibility were obtained.

EXAMPLE 3

Figure 7:
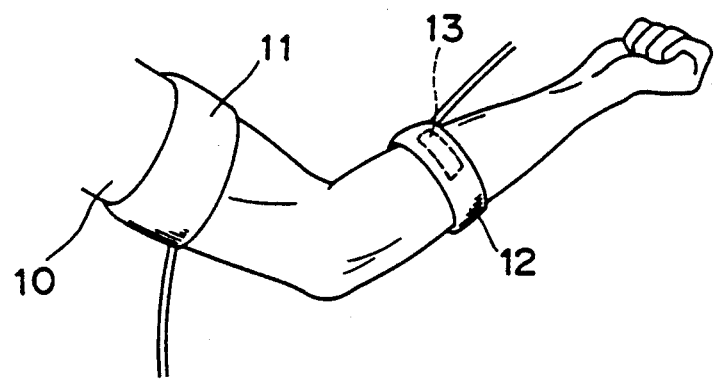
FIG. 7 is a perspective view illustrating how to execute a measurement with the use of the apparatus for measuring the inside information of substance in accordance with the present invention.

As shown in FIG. 7, an arm 10 was placed on a table in a quiet manner, a tourniquet 11 attached to a tonometer was put on the upper arm portion and an arm band 12 incorporating a measuring device 13 (to be discussed later) was put on and secured to the front arm portion with the measuring unit of the measuring device 13 applied to the inner side of the arm 10. Care was taken such that the venous blood vessels of the arm 10 do not exist between the projector and the light receiver.

The measuring device 13 included one light receiver and nine LEDs. The LEDs were disposed as separated by about 0.5 cm from one another, and as separated by about 4 cm from the light receiver. Each LED was lighted for 10 msec. and came ON in order. Each lightening cycle was equal to about 100 msec. After repetition of 50 lightening cycles, i.e., 5 seconds, one data was obtained. There were applied a method of obtaining the molecular absorption coefficients based on the logarithm of the light reception amount ratio above-mentioned, and a method of obtaining the molecular absorption coefficients based on the difference between the light reception amounts. Data were respectively obtained by these methods.

First, 10 data were obtained by measurement for 50 seconds with the tourniquet 11 loosened. Then, 15 data were obtained by measurement for 75 seconds with the tourniquet 11 fastened (at about 260 mm Hg) to stop the flow of blood. Then, 15 data were obtained by measurement for 75 seconds with the tourniquet 11 released. Such measurements were carried out for the total number of 8 persons.

Figure 8:
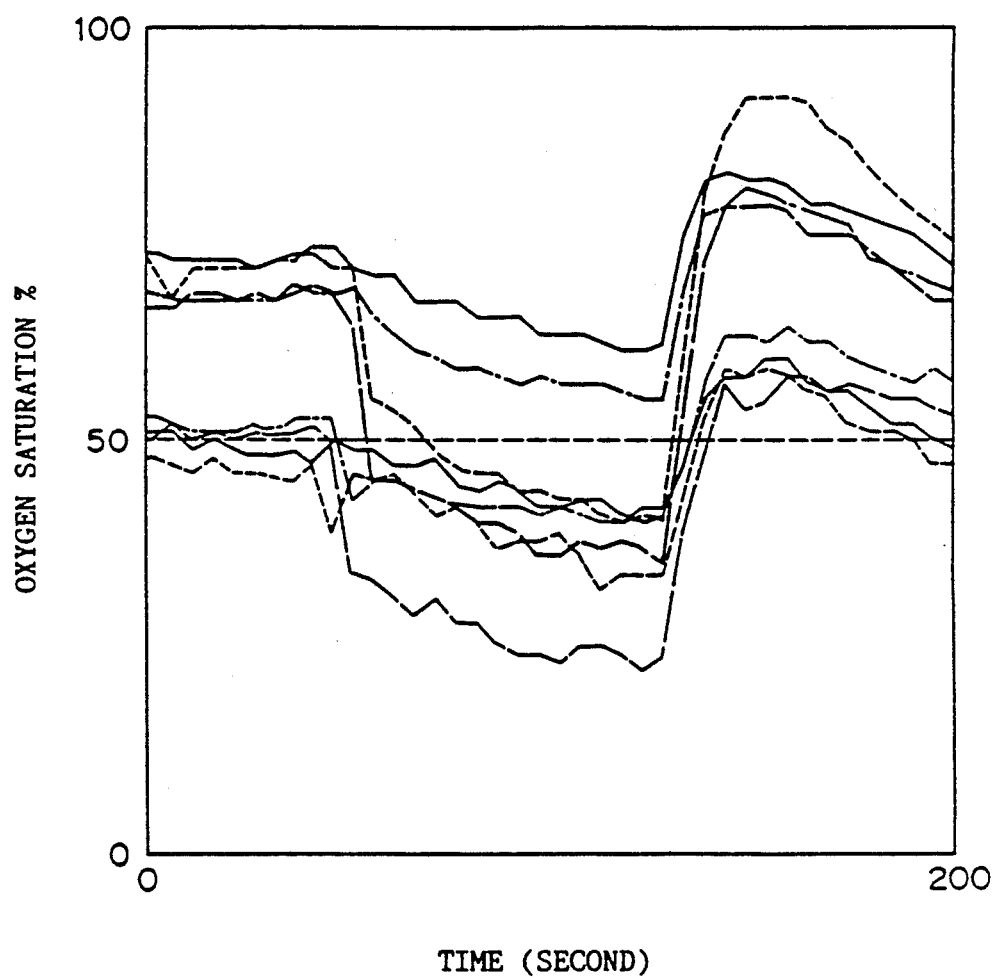
FIG. 8 and FIG. 9 are graphs illustrating measurement results before and after arrest of bleeding.
Figure 9:
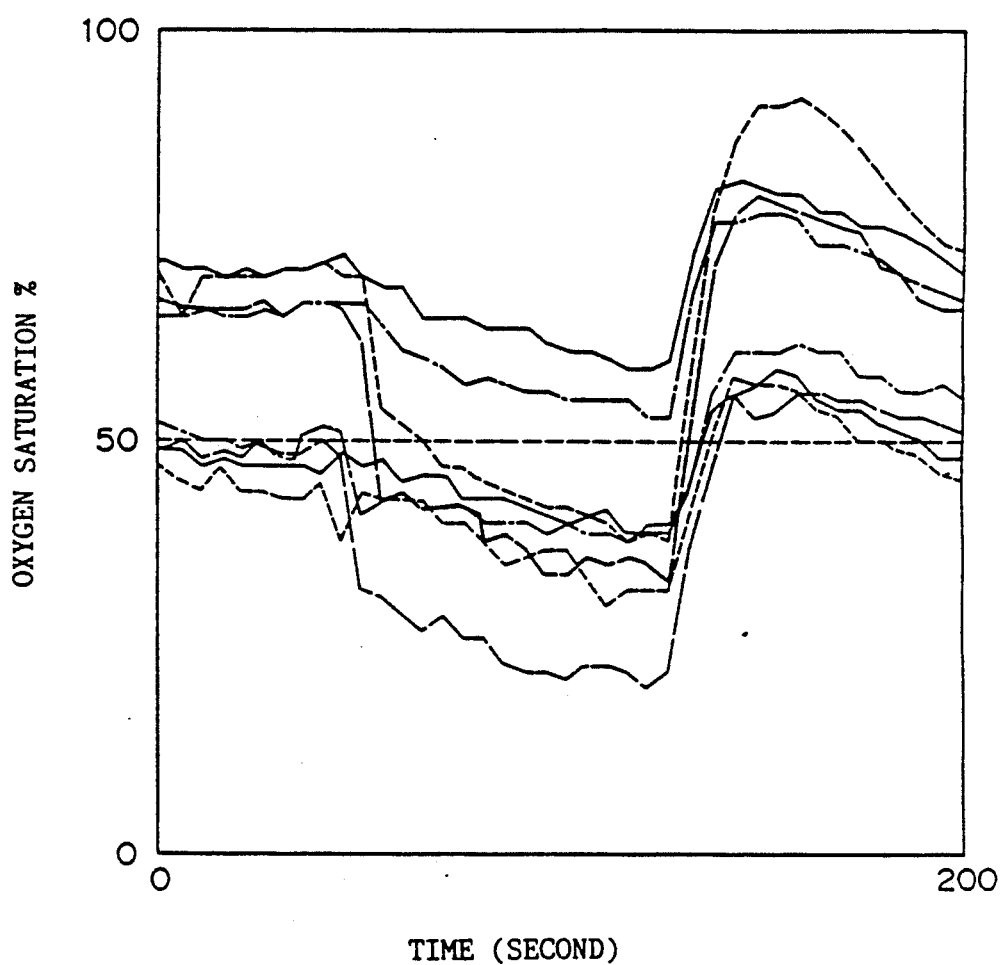

FIGS. 8 and 9 show the results of the measurements above-mentioned. FIG. 8 is a graph showing the results of the measurements made by the method of obtaining the molecular absorption coefficients based on the logarithm of the light reception amount ratio, while FIG. 9 is a graph showing the results of the measurements made by the method of obtaining the molecular absorption coefficients based on the difference of the light reception amounts. Each of FIGS. 8 and 9 shows eight turned lines which respectively correspond to the data of 8 persons.

There are substantially no difference in data between the measurements made by both calculating methods.

The degree of oxygen saturation is once lowered after the bleeding has been arrested (after 50 seconds), and then abruptly increased after the arrest of bleeding has been released (after 125 seconds). Such a trend commonly appears on the data of all the persons even though there are some differences among the individuals. Accordingly, it may be considered that the degrees of oxygen saturation were measured with good reproducibility.

EXAMPLE 4

Measurements were made on the same person at the same measuring point thereof (the arm inner side) with no bleeding arrested, twice every day at the same times (10 o'clock and 16 o'clock) in the morning and in the afternoon, with the use of the measuring device 13 mentioned earlier. Such measurements were made for 6 days. At each measurement, 30 data were obtained, of which 20 data were plotted.

Figure 10:
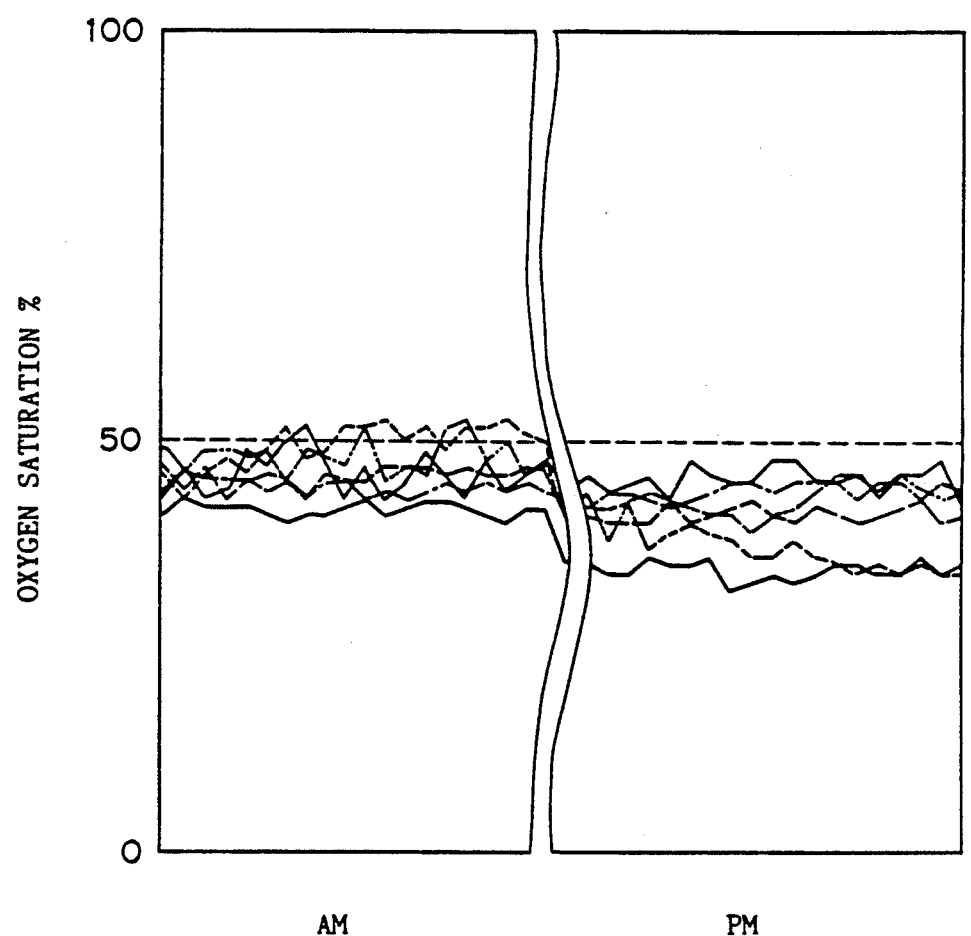
FIG. 10 and FIG. 11 are graphs illustrating the results of measurements made on the same person at different times.
Figure 11:
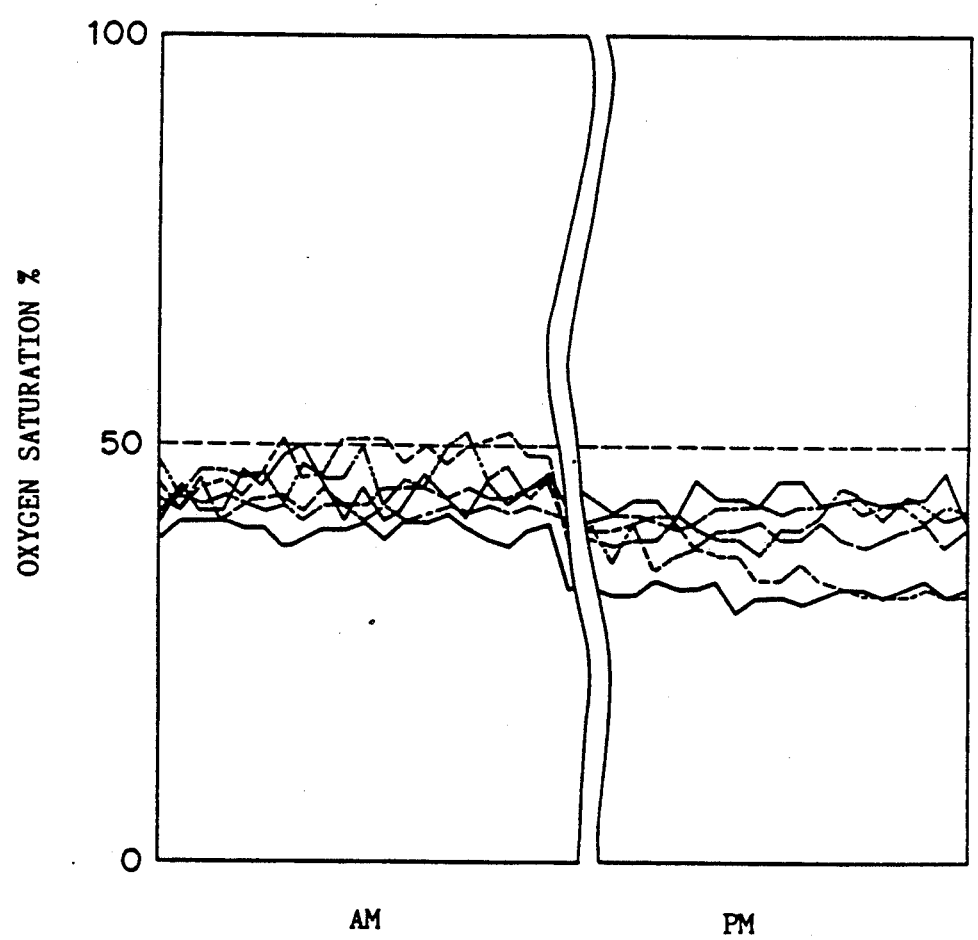
Figure 12:
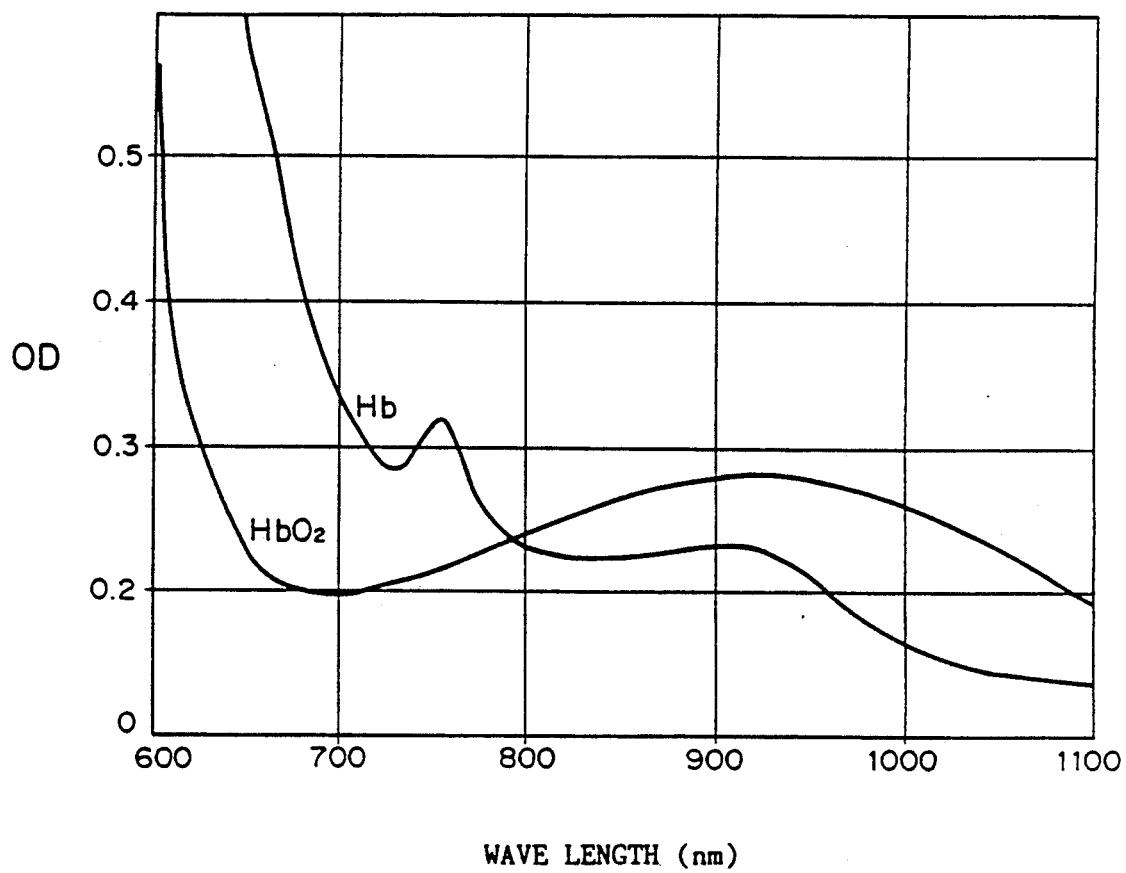
FIG. 12 is a graph illustrating the light absorption spectra of $HbO_2$ and Hb.

The measurement results are shown in FIGS. 10 and 11, in each of which total 12 turned lines respectively show the data of two measurements of six days. It is apparent from FIGS. 10 and 11 that the degrees of oxygen saturation measured in the morning are substantially the same, and the degrees of oxygen saturation measured in the afternoon are also substantially the same. Further, it is apparent from FIGS. 10 and 11 that the degrees of oxygen saturation in the morning are considerably different from those in the afternoon. Thus, the variations of the measurement results are small to prove the reliability of the data.

WHAT WE CLAIM IS:

1. A method of measuring the inside information of substance with the use of light scattering, comprising the steps of:
   successively irradiating lights at a plurality of irradiation points which are disposed substantially in the same direction with respect to a light receiving point on the surface of substance, wherein substantial optical diffusion paths from said irradiation points to said light receiving point being different in length from one another, and wherein a distance between each pair of said irradiation points being shorter in length than a length of each of said optical diffusion paths;
   receiving the irradiated lights at said light receiving point;
   executing a predetermined calculation based on the difference of light reception data corresponding to the respective irradiations; and
   determining, from a result of said predetermined calculation, the inside information of said substance.

2. Apparatus for measuring the inside information of substance with the use of light scattering, comprising:
   light irradiating means for irradiating lights at a plurality of irradiation points disposed substantially in the same direction with respect to a light receiving point on a surface of substance, wherein substantial optical diffusion paths from said irradiation points to said light receiving point being different in length from one another, and wherein a distance between each pair of said irradiation points being shorter in length than a length of each of said optical diffusion paths;
   light receiving means for receiving the irradiated light at said light receiving point; and
   data processing means for executing a predetermined calculation based on the difference of light reception data, thereby to determine the inside information of said substance.

3. Apparatus for measuring the inside information of substance with the use of light scattering as set forth in claim 2, wherein the light receiving point and the irradiation points are disposed on the same side of the surface of the substance.

4. Apparatus for measuring the inside information of substance with the use of light scattering as set forth in claim 2, wherein the light receiving point and the irradiation points are respectively disposed on the opposite sides of the surfaces of the substance.

5. A method of measuring the inside information of substance with the use of light scattering, comprising the steps of:
   irradiating light from an irradiation point on a surface of substance;
   receiving said light at a plurality of light receiving points disposed substantially in the same direction with respect to said light irradiation point, wherein substantial optical diffusion paths from said irradiation point to said light receiving points being different in length from one another, and wherein a distance between each pair of said light receiving points being shorter in length than a length of each of said optical diffusion paths;
   executing a predetermined calculation based on the difference of light reception data at said light receiving points; and
   determining, from a result of said predetermined calculation, the inside information of said substance.

6. Apparatus for measuring the inside information of substance with the use of light scattering, comprising:
   light irradiating means for irradiating light at an irradiation point on a surface of substance;
   light receiving means for receiving said light at light receiving points disposed substantially in the same direction with respect to said light irradiation point, wherein substantial optical diffusion paths from said irradiation point being different in length from one another, and wherein a distance between each pair of said light receiving points being shorter in length than a length of each of said optical diffusion paths; and
   data processing means for executing a predetermined calculation based on the difference of light reception data at said light receiving points, thereby to determine the inside information of said substance.

7. Apparatus for measuring the inside information of substance with the use of light scattering as set forth in claim 6, wherein the light receiving point and the irradiation points are disposed on the same side of the surface of the substance.

8. Apparatus for measuring the inside information of substance with the use of light scattering as set forth in claim 6, wherein the light receiving point and the irradiation points are respectively disposed on the opposite sides of the surfaces of the substance.

* * * * *